United States Patent [19]

Hirvela

[11] 4,374,571
[45] Feb. 22, 1983

[54] SCENT DISPENSER

[76] Inventor: George T. Hirvela, 6816 Tower Ave., Superior, Wis. 54880

[21] Appl. No.: 236,311

[22] Filed: Feb. 20, 1981

[51] Int. Cl.³ .......................... A24F 25/00; A61L 9/04
[52] U.S. Cl. ...................................... 239/36; 206/0.5; 206/37; 220/69; 239/56; 239/57
[58] Field of Search .................... 206/0.5, 38, 37; 239/36, 57 X, 58, 56 X; 220/212, 69; 215/100 R

[56] References Cited

U.S. PATENT DOCUMENTS

| | | | |
|---|---|---|---|
| 1,732,028 | 10/1929 | Reiner | 239/36 |
| 2,640,626 | 6/1953 | Newell | 220/69 |
| 2,959,354 | 11/1960 | Beck | 239/36 |
| 3,134,544 | 5/1964 | Copley | 239/55 |

*Primary Examiner*—William T. Dixson, Jr.
*Attorney, Agent, or Firm*—Merchant, Gould, Smith, Edell, Welter & Schmidt

[57] ABSTRACT

A device (10) for dispensing a scent is disclosed which includes a container (12) having a first end (13) with an opening (16) therein and a second closed end (14). The scent is held in an absorbent body of material (20) which is disposed within the interior of the container (12). Retaining means (25) releasably holds the scent-holding body (20) within the container (12). A cover (30) is provided which can be secured upon either end (13, 14) of the container (12) in a manner enclosing that portion of the container. A sealing ring (40) and sealing disc (44) prevent the scent from being released when the cover (30) encloses the opening end (13) of the container (12).

5 Claims, 7 Drawing Figures

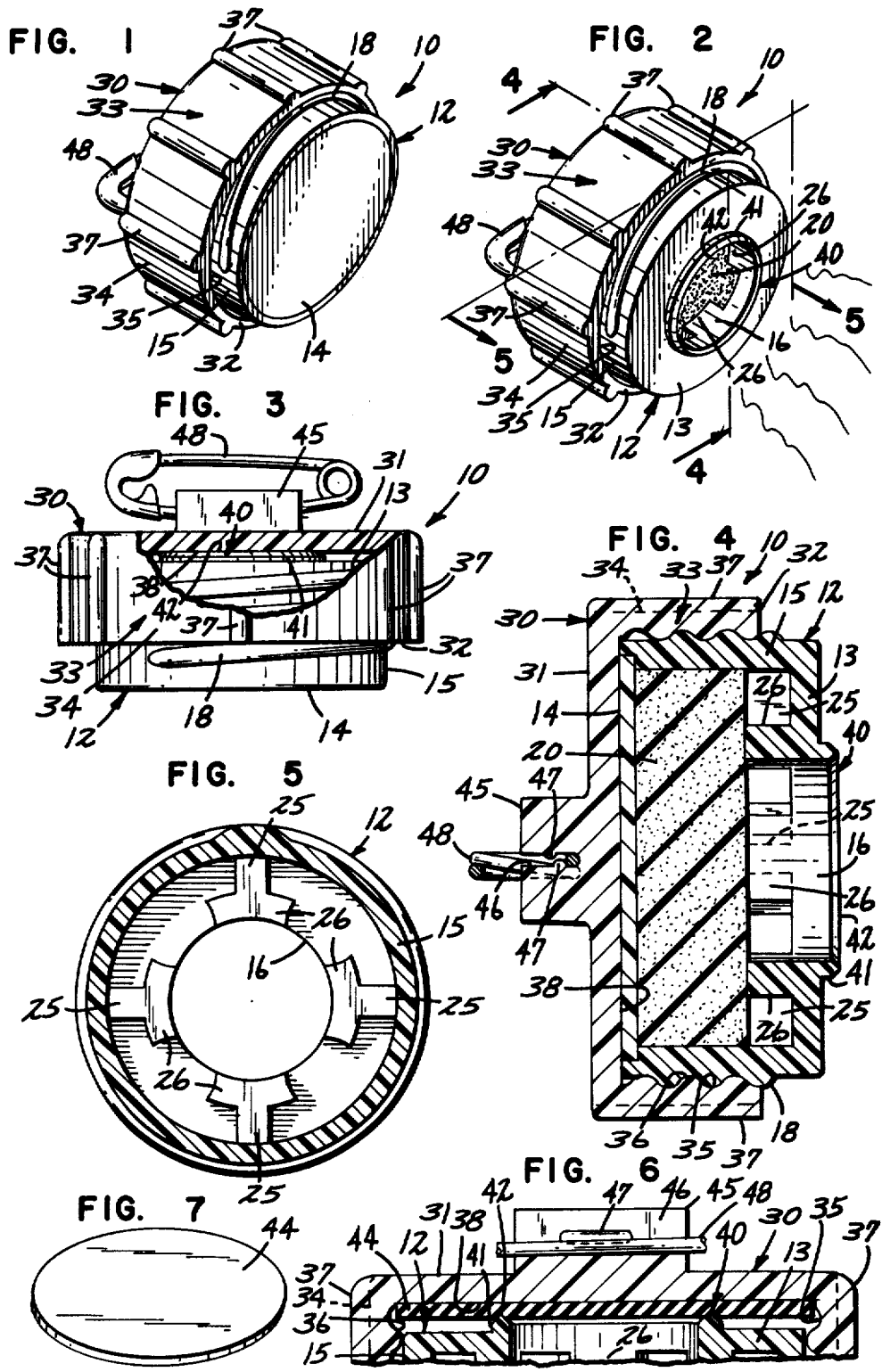

SCENT DISPENSER

TECHNICAL FIELD

The present invention relates to devices for dispensing scents and more particularly to scent dispensers used in hunting, trapping, and other wildlife activities.

BACKGROUND OF THE INVENTION

Almost all hunters and trappers use some means for masking or eliminating their ever present human scent in order to be able to move as close to the prey as possible. Generally, a concentrated solution, such as the scent of a deer, is applied directly to a portion of the hunter's clothing or to a separate item which can be somehow secured to the hunter. As the hunter proceeds through the woods or field, the artificial scent is left in his trail, thereby masking or disguising any characteristic human scent which would otherwise have been the noticeable scent left behind. Animal scents are also used to attract animals as well as to mask a person's scent, and are used by wildlife photographers and other nature enthusiasts in addition to hunters and trappers.

Whatever the specific use, artificial scents are a necessary item for most if not all users to achieve successful results in their hunting, trapping, or other outdoor activities. Prior art devices for dispensing animal scents have oftentimes proven unsatisfactory for various reasons. One type of prior art is the use of a simple sponge or pad attached to a piece of plastic. The plastic piece is securable to the user's clothing. However, there is no cover provided to enclose the saturated sponge or pad when the scent is no longer needed. The scent then becomes an offensive odor as it continues to be released in the hunter's vehicle or home, unless the pad is immediately disposed of or cleaned after each use. Another prior art device uses a cover which screws down around the scented body shutting off the odor. However, as the cover is unscrewed and the scent-carrying body is exposed, not only is the scent released but undesirable dripping of the scented liquid occurs if the user accidentally over-saturates the pad.

What is needed then is a scenting device which eliminates the mess of the old devices, is long lasting, reusable and convenient, and provides a dependable seal whenever the user desires to prevent the release of the scent. The present invention answers these needs and provides other benefits which will be detailed below.

SUMMARY OF THE INVENTION

The present invention is a device designed to dispense a scent and includes a container having a generally hollow interior, a side wall, a closed end, and an end with an opening. Deposited within the container is a sponge-like body which holds the scent. Retaining members projecting from the periphery of the opening into the container interior releasably retain the scent-holding body within this container. A cover is also provided which can be secured over either end of the container to either seal the container to prevent loss of the scent or to permit the scent to escape from the container through the container's opening. The cover also includes means for securing the entire device to a separate object.

According to one aspect of the present invention, there is provided a scent dispensing device having a cover designed to be positioned on the container of the device so as to allow either the release of the scent from the container or the sealing of the scent within the container.

According to another aspect of the present invention, a scent holding body is provided which can be removed from the device and easily returned to the interior of the container for further use.

A further aspect of the invention provides a means for securing the entire device to a separate object such as a hunter's outer clothing or a bush.

BRIEF DESCRIPTION OF THE DRAWINGS

FIG. 1 is a perspective view of the present invention showing the elements of the invention in sealing relation.

FIG. 2 is a perspective view of the present invention showing the elements of the invention in a scent releasing relation.

FIG. 3 is a top plan view of the present invention as seen in FIG. 1, with portions broken away and shown in cross-section.

FIG. 4 is a cross-sectional view of the present invention as seen along line 4—4 of FIG. 2.

FIG. 5 is a cross-sectional view of the present invention as seen along line 5—5 in FIG. 2.

FIG. 6 is a partial cross-sectional view of the present invention in sealing relation.

FIG. 7 is a perspective view of a portion of the present invention.

DETAILED DESCRIPTION OF THE PREFERRED EMBODIMENT

Referring now to the drawings wherein like reference numerals refer to the same aspect of the invention throughout the several views, FIGS. 1 and 2 illustrate the present invention and its two modes of use. In FIG. 1, the parts of the invention are in sealing relation with respect to each other. In FIG. 2, the parts are positioned so that a scent contained in the device 10 can be released from the device. These two relationships will be discussed in further detail after the following discussion of the various individual parts of the device 10, herein referred to as the scent dispenser.

The central aspect of the scent dispenser 10 is a container 12 having a generally circular cross-section and a substantially hollow interior. The interior of the container is defined by a first end 13, a second end 14, and a cylindrical side wall 15. The second end 14 is completely closed. The first end 13 has a centrally located opening 16 as can be seen in FIG. 2. The cylindrical side wall 15 extends between the first end 13 and the closed second end 14. Extending along the outer surface 17 of the side wall 15 is a continuous raised surface portion 18 forming a generally helical pattern. See FIGS. 3 and 4. The raised surface portion 18 is designed to be threaded with another raised surface portion for purposes to be discussed further below. The raised surface portion 18 of the side wall 15 extends substantially from end to end of the side wall 15.

As partially seen in FIG. 2 and more definitely illustrated in FIG. 4, a means for holding a scent, e.g., a deer, bear, moose, or skunk scent, commercially available in concentrated liquid form, is placed within the interior of the container 12. In the preferred embodiment, the scent holding means is a sponge-like body or pad of absorbent material 20, capable of being saturated with the scent. Whatever type of absorbent material is used, it must have a flexible construction in order to be inserted into and removed from the container 12 through the first end opening 16. The absorbent material or pad 20 is reusable and should be of the type easily cleaned with plain water.

Means cooperating with the container 12 releasably hold the scent holding pad 20 within the container interior. The retaining means in the preferred embodiment is shown as a plurality of retaining members or ribs 25 projecting into the interior of the container 12 from locations along the periphery of the container opening 16. See FIGS. 2 and 4. Each member or rib 25 has an end portion 26 which terminates at a point intermediate the container's first end 13 and second end 14 as shown in FIG. 5. The retaining members 25 hold the scent holding material or pad 20 away from direct contact with the first end 13 of the container 12. A space is then provided within the container interior between the container's first end 13 and the surface of the scent holding material nearest the container's opening 16. This space allows the scent to build up within the container and then be more effectively released from the container opening 16.

The cover 30 for the container 12 serves also as a backing for the container during the scent releasing time of use. The cover has a generally circular cross-section, and it is designed with a diameter size large enough to enclose an end portion of the container 12, as shown in FIGS. 1-4. The cover 30 has a closed or solid end 31, an open end 32 and a cylindrical side wall 33 extending between the two ends 31, 32. The cylindrical side wall 33 has an outer surface 34 and an inner surface 35. Referring now to FIG. 4, means for securing the cover 30 to the container 12 are located on the interior surface 35 of the cover side wall 33. This securing means includes a second continuous raised surface portion 36 which forms a helical pattern. The raised surface portion 36 extends substantially the full width of the side wall 33. The two helical patterns of raised surface portions 18, 36, one on the container side wall 15 and the other on the cover side wall outer surface 34, respectively, are constructed to be threaded together so that the surfaces mate with respect to each other as shown in FIG. 4. Also, the helical patterns are designed to allow the cover 30 to be threaded onto the container 12 in a direction originating from either end 13, 14 of the container 12, as illustrated by FIGS. 1 and 2. It is this type of securing means which allows the scent dispenser 10 to be sealed or open as determined by which end of the container 12 the cover 30 presently encloses.

Also as seen in FIGS. 1 and 2, a plurality of spaced apart, substantially elongated raised surface portions 37 are located along the outer surface 34 of the cover side wall 33. This arrangement provides a gripping means for the user as he or she threads the cover 30 onto or off the respective container end portions 13, 14.

The container 12 also includes means for preventing the escape or release of the scent from the container 12 when the cover 30 is enclosing the container opening end 13. The preventing means is a sealing ring 40 projecting outwardly from the periphery of the container opening 16. The ring 40 has a generally circular end edge 41 with a raised surface portion 42. The raised surface portion 42 is designed to contact and seal against the cover inner surface 38 when the container first end 13 is enclosed by the cover 30. See FIG. 3. To ensure an even tighter seal when the scent being held in the container is quite offensive, e.g., skunk scent, an additional sealing element can be used. This element is a sealing disc 44, shown in FIG. 7, which is disposed between the cover end 31 and the container sealing ring 40, shown in FIG. 6. The disc 44 is substantially equal in size to the area of the inner surface of the cover closed end 31. Its size allows it to be snapped into the cover flush against the interior surface 38 of the closed end 31 and held in place by a segment of the cover raised surface portion 36. The sealing disc 44 can be made of either solid rubber, soft plastic, or another suitable sealing material. As can be seen in FIG. 6, the raised surface portion 42 of the sealing ring 40 protrudes into the sealing disc 44 and together the ring and disc prevent any scent from accidentally seeping out of the enclosed container opening 16.

Also provided on the scent dispenser 10 are means for attaching the dispenser 10 to a separate object. In the preferred embodiment, the particular means chosen to illustrate this aspect of the invention is a locking block/safety pin combination. As seen most clearly in FIGS. 3 and 4, the locking block 45 is a projecting portion of the outer surface of the cover solid end 31; however, the block 45 may be a separate item mounted to the cover end 31. The locking block 45 is substantially a rectangular, box-shaped element and has a slot 46 extending along the length of the element. The slot 46 has a bottom wall and two opposing side walls. A safety pin 48 is inserted into the slot and is retained within the slot by means of a pair of non-aligned, adjacent protrusions 47, seen most clearly in FIG. 4. The protrusions 47 cooperate with the slot to allow a narrow passageway for the safety pin 48 to be passed into and out of the locking block 45, yet the off-center arrangement of the protrusions 47 assures the pin 48 will not accidentally be released from the locking block. The pin 48, of course, is replaceable.

With the exception of the safety pin 48, the sealing disc 44, and the scent holding material 20, the other parts of the dispenser 10, the cover 30, the container 12, the retaining members 25, the sealing ring 40, and the locking block 45 are all made from molded plastic. Many types of plastic materials would be suitable for the purposes of the invention, however, it should be a type which will endure usage in various outdoor weather conditions.

To use the scent dispenser, a small amount of a scent is poured into the container opening 16 onto the pad 20 and allowed to penetrate and saturate the pad. With the cover 30 secured on the container second end 14 and the container opening 16 left exposed, the dispenser is then pinned to the user's outer clothing or on a bush near the user. Because the safety pin 48 can slide back and forth along the slot 46 there is sufficient room for a small tree branch or twig of a bush to be inserted through the pin and the dispenser is then fastened with the safety pin to the bush or tree.

Should the pad 20 be accidentally over-saturated it can be easily removed from the container interior and the excess scent discarded. To remove the pad 20 merely requires the use of a relatively sharp instrument, e.g., a pocket knife or a stick, to pull an edge of the pad 20 past an end of one of the retaining members 25. The pad edge is then lifted into the opening 16 and pulled out of the container 20 through the opening 16. The pad 20 is replaced by squeezing or otherwise reducing the size of the pad so that it can be pushed back through the container opening 16, past the ends of the retaining members 25 and then arranged within the interior of the container. The pads are also replaceable.

The cover 30 threads onto either the first end 13 or the second end 14 of the container 20. When the user does not want the scent to be released, the cover is threadably removed from the second end 14 of the container and threaded onto the container first end 13. The container will then be sealed and no scent can be released. See FIGS. 1, 3, and 6. The raised surface portions 37 of the cover side wall 33 allow the user to firmly grip the cover 30 and loosen it from the respective container end portion.

Because the dispenser can be pinned or secured onto the use's clothing and subsequently removed therefrom, the dispenser eliminates applying the scent directly to the clothing and thus eliminates a significant amount of inconvenience which accompanies such applications.

The reversible cover 30 which threads onto either end 13, 14 of the container 12 assures that the cover 30 will not be misplaced whether the dispenser 10 is being used or not.

The scent holding means 20 is removable, reusable and easily cleaned for future uses or for use with a different scent.

Whether in use or not, the space created by the retaining members 25 between the container's first end 13 and the scent holding means 20 allows a quick and complete saturation of the material as well as providing room for the scent to "build up" for dispensing through the opening 16. The build-up continues in the space even during the time the scent is being released through the exposed opening 16.

With the double sealing aspect, the dispenser when not in use can be safely carried on the user's person or in a vehicle without worry that the scent will be released and offend others or create an unpleasant breathing environment.

Numerous characteristics and advantages of the invention have been set forth in the foregoing description, together with the details of the structure and function of the invention. The novel features thereof have also been pointed out in the appended claims. The disclosure, however, is illustrative only and changes may be made in detail especially in matters of shape, size and arrangement of some of the parts, within the principle of the invention, to the full extent indicated by the broad general meaning of the terms expressed in the following claims.

What is claimed is:

1. An animal scent holding and releasing device for outdoor use, comprising:
   (a) a container having a continuous side wall, a first end having an opening therein, and a closed second end opposite said first end, said container having a generally circular cross-section;
   (b) means removably disposed within said container for holding a scent;
   (c) means associated with said container for releasably retaining said scent holding means within said container, said retaining means including a plurality of retaining members projecting from said container first end adjacent said opening in a direction towards said second end, each of said retaining members having a free end terminating at a location intermediate said container first and second ends, said scent holding means being a sponge-like body of absorbent material capable of holding a scent, said body being disposed between and engaged by said retaining member ends and said container second end, said body of material being flexible whereby said body may be inserted into and removed from said container through said first end opening;
   (d) a cover constructed and designed to enclose either of said container ends;
   (e) means for securing said cover to either said first end for sealing said container to prevent loss of the scent carried therein, or to said second end to permit the scent to be released from said container through said first end opening, said securing means including a pair of mating surfaces, one of said mating surfaces being located on said cover and the other mating surface being located on said container, each of said mating surfaces including raised surface portions,
   said cover having a generally circular cross-section, a solid end, an open end and a continuous side extending therebetween, said side having an inner surface and an outer surface, said inner surface containing said respective raised surface portions, said cover raised surface portions being designed to be threaded upon said respective raised surface portions on said container side wall in a direction originating from either of said container ends; and
   (f) means disposed on said cover solid end for attaching said device to a separate object.

2. The device according to claim 1 including a locking block disposed on said closed second end and a replaceable safety pin disposed in said locking block.

3. The device according to claim 1 further including means for preventing the release of the scent from said container, said means including a sealing ring projecting outwardly from the periphery of said container opening, said ring designed to seal against an inner surface of said closed second end when said cover encloses said container first end.

4. The device according to claim 1 further including a sealing ring projecting outwardly from said container first end around said opening and a closed sealing disk disposed intermediate said second end and said sealing ring.

5. A device for dispensing a scent comprising:
   (a) a container having a generally circular cross-section and a hollow interior, including a first end having a portion with an opening therein, a closed second end, a plurality of retaining members projecting from said first end around said opening into said interior, each retaining member having an end terminating at a location intermediate said first end and said second end, and a cylindrical side extending between said first and second ends, said cylindrical side having raised surface portions arranged in a helical pattern;
   (b) a body of absorbent material designed to hold a scent, said body being disposed intermediate said retaining member ends and said closed second end and having a flexible construction for insertion into and removal from said container interior through said first end opening;
   (c) a cover designed to enclose a portion of said container, said cover having a generally circular cross-section, a solid end, an open end and a cylindrical side extending therebetween, said cylindrical side having an inner surface and an outer surface, said inner surface having raised surface portions designed to thread with said container raised surface portions in a direction originating from either of said container ends;

(d) means, disposed on an outer surface of said cover solid end, for attaching said device to a separate object, said means including a locking block and a replaceable safety pin disposed in said locking block, said locking block having a slot with opposing walls and a protrusion extending from each of said side walls, said protrusions being located adjacent each other and cooperating with said slot to provide a narrow passageway therebetween, said slot and said protrusions restricting said safety pin in said locking block while allowing the removal and insertion of said pin from said block through said narrow passageway;

(e) means for preventing the release of the scent from said container including a sealing ring projecting outwardly from the periphery of said container opening, said ring including an end edge having a surface portion designed to contact and seal against an inner surface of said cover when said cover encloses said container first end; and (f) a substantially flat sealing disc substantially equal in diameter to that of said cover solid end, said disc being disposed intermediate said solid end and said sealing ring when said cover encloses said container first end.

* * * * *